United States Patent
Baker et al.

(10) Patent No.: US 8,865,465 B2
(45) Date of Patent: Oct. 21, 2014

(54) POLYMER MATRICES FOR CELL CULTURE

(75) Inventors: Wendy Annette Baker, Bath, NY (US); Theresa Chang, Painted Post, NY (US); Robert Randall Hancock, Jr., Corning, NY (US)

(73) Assignee: Corning Incorporated, Corning, NY (US)

( * ) Notice: Subject to any disclaimer, the term of this patent is extended or adjusted under 35 U.S.C. 154(b) by 305 days.

(21) Appl. No.: 13/270,357

(22) Filed: Oct. 11, 2011

(65) Prior Publication Data

US 2012/0178162 A1    Jul. 12, 2012

Related U.S. Application Data

(60) Provisional application No. 61/430,755, filed on Jan. 7, 2011.

(51) Int. Cl.

| | | |
|---|---|---|
| C12N 5/071 | (2010.01) | |
| C08F 120/18 | (2006.01) | |
| C09D 133/14 | (2006.01) | |
| C09D 133/06 | (2006.01) | |
| C08J 3/075 | (2006.01) | |
| C09D 101/26 | (2006.01) | |
| C09D 101/28 | (2006.01) | |
| C12N 5/00 | (2006.01) | |
| C08L 1/28 | (2006.01) | |
| C08L 1/26 | (2006.01) | |

(52) U.S. Cl.
CPC ........ C09D 133/066 (2013.01); *C12N 2533/78* (2013.01); *C12N 2533/10* (2013.01); C09D 133/14 (2013.01); *C08J 2301/26* (2013.01); *C08L 1/284* (2013.01); *C12N 2537/10* (2013.01); *C12N 2533/30* (2013.01); C08J 3/075 (2013.01); C09D 101/26 (2013.01); C09D 101/284 (2013.01); C12N 5/0068 (2013.01); *C08L 1/26* (2013.01)
USPC ........................................ 435/370; 526/329.7

(58) Field of Classification Search
None
See application file for complete search history.

(56) References Cited

U.S. PATENT DOCUMENTS

| | | | |
|---|---|---|---|
| 6,300,390 B1 | 10/2001 | Angeletakis | 523/116 |
| 7,144,453 B2 | 12/2006 | Yim et al. | 106/122 |
| 2005/0059140 A1* | 3/2005 | Liebmann-Vinson et al. | 435/289.1 |
| 2005/0279730 A1* | 12/2005 | Miyake et al. | 216/41 |
| 2009/0227024 A1* | 9/2009 | Baker et al. | 435/378 |
| 2009/0227027 A1* | 9/2009 | Baker et al. | 435/406 |
| 2011/0053270 A1 | 3/2011 | Chang et al. | 435/402 |

OTHER PUBLICATIONS

Alekh, S., et al., "Surface Modification of Polycarbonate by Ultraviolet Radiation and Ozone", The Journal of Adhesion, 1545-5823, vol. 83, 1, (2007), pp. 43-66.

Zhang, L.-M., "Cellulosic Associative Thickners", Carbohydrate Polymers, 45, (2001), pp. 1-10.

(Continued)

*Primary Examiner* — Melvin C Mayes
*Assistant Examiner* — Stefanie Cohen
(74) *Attorney, Agent, or Firm* — John L. Haack

(57) ABSTRACT

Synthetic cell culture surfaces, including a hydrophobe modified cellulose or an hydroxylated acrylate polymer composition and optionally including a silica source, cell culture coating and cell culture articles incorporating the composition, and methods of making and using the articles for cell culture, as defined herein.

15 Claims, 9 Drawing Sheets

(56) References Cited

OTHER PUBLICATIONS

Samuneva, et al., "Sol-Gel Synthesis and Structure of Silica Hybrid Biomaterials", Journal of Non-Crystalline Solids, 354, (2008), pp. 733-740.

Jang, et al., "Formation and Structure of Polyacrylamide-Silica Nancomposites by Sol-Gel Process", Journal of Applied Polymer Science, vol. 83, (2002), pp. 1817-1823.

Ren, et al., "Synthesis and Characterization of Gelatin-Siloxane Hybrids Derived Through Sol-Gel Procedure", Journal of Sol-Gel Science and Technology, 21, (2001), pp. 115-121.

Toki, et al., "Structure of Poly(Vinylpyrrolidone)-Silica Hybrid", Polymer Bulletin, 29, (1992), pp. 653-660.

Nakanishi, et al., "Phase Separation in Silica Sol-Gel System Containing Polyacrylic Acid", Journal of Non-Crystalline Solids, 139, (1992), pp. 1-3.

Park, et al., "Preparation and Optical Properties of Silica-Poly(Ethylene Oxide) Hybrid Materials", Journal of Sol-Gel Science and Technology, 16, (1999), pp. 235-241.

Shchipunov, et al., "A New Precursor for the Immobilization of Enzymes Inside Sol-Gel-Derived Hybrid Silica Nanocomposites Containing Polysacharides", Journal of Biochemical and Biophysical Methods, 58, (2004), pp. 25-38.

Coradin, et al., "Synthesis and Characterization of Alginate/Silica Biocomposites", Journal of Sol-Gel Science and Technology, 26, (2003), pp. 1165-1168.

Silva, et al., "Functional Nanostructured Chitosan-Siloxane Hybrids", Journal of Materials Chemistry, 15, (2005), pp. 3952-3961.

Lei, et al., "Soft Mold-Dry Etch: A Novel Hydrogel Patterning Technique for Biomedical Applications", Proc. $26^{th}$ Annual International Conference, IEEE EMBS, (2004), pp. 1983-1986.

\* cited by examiner

3A

3B

3C

3D

4A

4B

4C

4D

POLYMER MATRICES FOR CELL CULTURE

CROSS-REFERENCE TO RELATED APPLICATION(S)

This application claims the benefit of priority under 35 U.S.C. §119 of U.S. Provisional Application Ser. No. 61/430,755 filed on Jan. 7, 2011, the content of which is relied upon and incorporated herein by reference in its entirety.

CROSS-REFERENCE TO COPENDING APPLICATION

This application is related to commonly owned and assigned copending application U.S. Ser. No. 61/237,098, filed Aug. 26, 2009.

BACKGROUND

The disclosure relates to methods and articles for cell culture.

SUMMARY

The disclosure provides a non-animal derived cell culture system for the culture of mammalian cells. The cell culture system comprises water insoluble polymeric matrices or silica hybrids of modified water soluble, swellable polymers including, for example, modified cellulose.

BRIEF DESCRIPTION OF THE DRAWINGS

In embodiments of the disclosure.

DETAILED DESCRIPTION

Figure 1A:
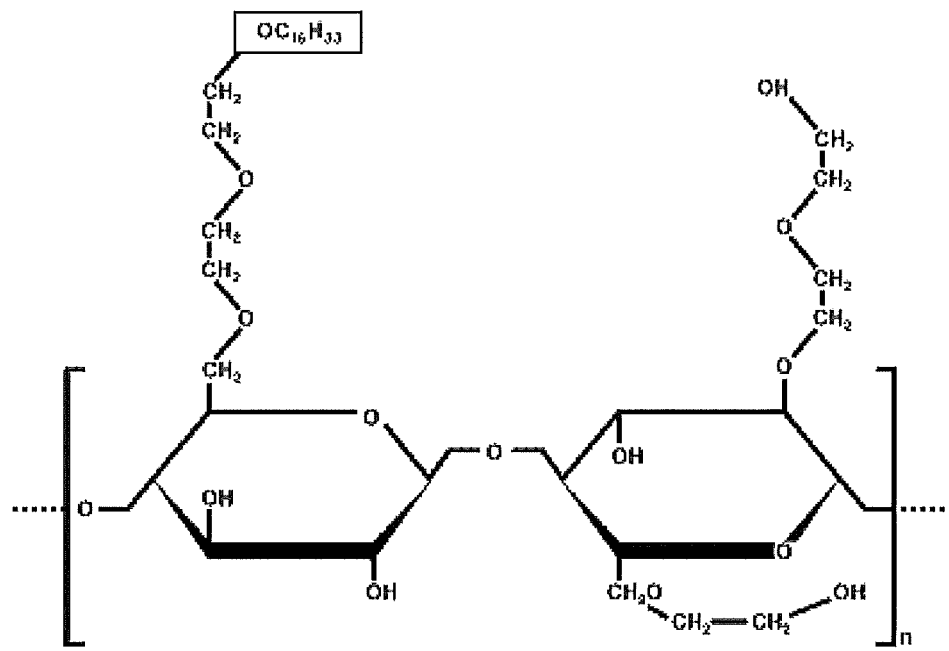
FIGS. 1A and 1B, respectively, show schematic representations of a hydrophobe modified hydroxyethylcellulose (HMHEC), and a representation of gel formation in solution via hydrophobic interactions between the hydrophobe alkyl side chains of the hydrophobe modified polysaccharide.

Various embodiments of the disclosure will be described in detail with reference to drawings, if any. Reference to various embodiments does not limit the scope of the invention, which is limited only by the scope of the claims attached hereto. Additionally, examples in this specification are not limiting and merely set forth some of the many possible embodiments for the claimed invention.

Abbreviations and Definitions

HEC—hydroxyethylcellulose

HMHEC—hydrophobe modified hydroxyethylcellulose (Aldrich or Aqualon)

HEMA—hydroxyethylmethacrylate

PS67—PolySurf 67 (a commercially available cellulose material from Aqualon)

TMOS—tetramethoxysilane (a silica source)

MTMS—methyl trimethoxysilane (a silica source)

GAPS—gamma-aminopropyltrimethoxysilane (a silica source)

5P—is a HEMA copolymer having 95 wt % HEMA and 5 wt % phosphate modified HEMA or HEMA-phosphate (negatively charged); HEMA-phosphate is 2-methyl-2-propenoic acid ethyl-2-phosphate ester 10P—is a HEMA copolymer having 90 wt % HEMA and 10 wt % phosphate modified HEMA or HEMA-phosphate.

"Cross-link," "cross-linkable," "cross-linking," and like terms as used herein can refer to a decreased water solubility transformation, an increased viscosity transformation, decreased swelling transformation, or a combination thereof, of the initial coating composition leading to the final coating, when the initial coating is contacted with, for example, an UV-ozone source, or when a silica source is included in the initial coating formulation and allowed to chemically interact with the polymer component. UV-ozone surface modification methods for polymers are generally known, see for example, Surface Modification of Polycarbonate by Ultraviolet Radiation and Ozone, Alekh, S., et al., *The Journal of Adhesion*, 1545-5823, Vol. 83, 1, 2007, 43-66.

"Hydrogel" and like terms can refer a polymer that can absorb water in an amount of about 30% or more of its dry weight. In embodiments, a hydrogel can absorb water in about 100% or more of its dry weight. The amount of water that a hydrogel polymer can absorb can vary depending on the degree that the polymer is transformed, such as by crosslinking. Greater cross-linking often can lead to less water absorption or swelling.

"Carbohydrate" or like terms refer to any of various neutral compounds of carbon, hydrogen, and oxygen, such as sugars, starches, and celluloses. Cellulose refers to a polysaccharide $(C_6H_{10}O_5)_x$ of linked glucose units. Polysaccharide refers to a carbohydrate that can be decomposed by hydrolysis into two or more monosaccharide molecules; especially a polysaccharide, such as cellulose, starch, or glycogen, containing many monosaccharide units and marked by complexity.

"Coating," or like terms as used herein can be a noun (e.g., a coating composition on a surface or a coated article) or verb (e.g., applying or coating the composition on a substrate).

"Assay," "assaying," or like terms refer to an analysis to determine, for example, the presence, absence, quantity, extent, kinetics, dynamics, or type of a cell's response to an exogenous stimuli, such as a ligand candidate compound, culture media, substrate coating, or like considerations. The present disclosure mentions MTS assay and LDH assay. The MTS assay, for example, Promega MTS assay or CellTiter 96® Aqueous One Solution Cell Proliferation Assay, is a known colorimetric method for determining the number of viable cells in proliferation, cytotoxicity, or chemosensitivity assays (see Cat. No. G3580, www.promega.com). MTS Assays are performed by adding a small amount of the Cell- Titer 96® AQ$_{ueous}$ One Solution Reagent directly to culture wells, incubating for 1 to 4 hours and then recording absorbance at about 490 nm with a 96-well plate reader. The quantity of formazan product, as measured by the amount of 490 nm absorbance, is directly proportional to the number of living cells in culture. The Lactate Dehydrogenase Assay (LDH) assay (Promega CytoTox 96® Non-Radioactive Cytotoxicity Assay No. G1780, www.promega.com)) is a lysis assay and was performed to access cell attachment. The cells were lysed according to manufacturer's instructions and the amount of LDH released was measured, which measure is theoretically directly proportional to the number of cells present.

"Attach," "attachment," "adhere," "adhered," "adherent," "immobilized", or like terms generally refer to immobilizing or fixing, for example, a surface modifier film or like substance, a compatibilizer, a cell, a ligand candidate compound, and like entities of the disclosure, to a surface, such as by physical absorption, chemical bonding, and like processes, or combinations thereof. Particularly, "cell attachment," "cell adhesion," or like terms refer to the interacting or binding of cells to a surface, such as by culturing, or interacting of the cells with a surface, such as a biosensor surface or a culture well surface.

"Adherent cells" refers to a cell or a cell line or a cell system, such as a prokaryotic or eukaryotic cell, that remains associated with, immobilized on, or in certain contact with the outer surface of a substrate. Such type of cells after culturing can withstand or survive washing and medium exchanging process, a process that is prerequisite to many cell-based assays. "Weakly adherent cells" refers to a cell or a cell line or a cell system, such as a prokaryotic or eukaryotic cell, which weakly interacts, or associates or contacts with the surface of a substrate during cell culture. However, these types of cells, for example, human embryonic kidney (HEK) cells, tend to dissociate easily from the surface of a substrate by physically disturbing approaches such as washing or medium exchange. "Suspension cells" refers to a cell or a cell line that is preferably cultured in a medium wherein the cells do not attach or adhere to the surface of a substrate during the culture. "Cell culture" or "cell culturing" refers to the process by which either prokaryotic or eukaryotic cells are grown under controlled conditions. "Cell culture" also refers to the culturing of cells derived from multicellular eukaryotes, especially animal cells, but also to the culturing of complex tissues, organs, pathogens, or like systems.

"Cell" or like term refers to a small usually microscopic mass of protoplasm bounded externally by a semipermeable membrane, optionally including one or more nuclei and various other organelles, capable alone or interacting with other like masses of performing all the fundamental functions of life, and forming the smallest structural unit of living matter capable of functioning independently including synthetic cell constructs, cell model systems, and like artificial cellular systems.

"Cell system" or like term refers to a collection of cells and can include more than one type of cells (or differentiated forms of a single type of cell), which interact with each other, thus performing a biological, physiological, or pathophysiological function. Such cell system can include, for example, an organ, a tissue, a stem cell, a differentiated hepatocyte cell, and like cell systems.

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, and like abbreviations).

"Include," "includes," or like terms means including but not limited to.

"About" modifying, for example, the quantity of an ingredient in a composition, concentrations, volumes, process temperature, process time, yields, flow rates, pressures, and like values, and ranges thereof, employed in describing embodiments of the disclosure, refers to, for example, variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the claims appended hereto include equivalents to these quantities.

"Consisting essentially of" in embodiments refers, for example, to a composition, a method of making or using a composition, formulation, or coating composition on the surface of cell culture article, and like articles, devices, or apparatus of the disclosure, and can include the components or steps listed in the claim, plus other components or steps that do not materially affect the basic and novel properties of the compositions, articles, apparatus, and methods of making and use of the disclosure, such as particular reactants, particular additives or ingredients, a particular agent, a particular cell or cell line, a particular surface modifier or condition, a particular ligand or drug candidate, or like structure, material, or process variable selected. Items that may materially affect the basic properties of the components or steps of the disclosure or that may impart undesirable characteristics to the present disclosure include, for example, decreased affinity of the cell for the coated cell culture surface at the outset, decreased affinity of the substrate surface for the cell culture coating, abnormally decreased or increased affinity of a pathogen for a cultured cell, anomalous or contrary cell activity in response to a ligand candidate or like stimulus, and like characteristics.

The indefinite article "a" or "an" and its corresponding definite article "the" as used herein means at least one, or one or more, unless specified otherwise.

Specific and preferred values disclosed for components, ingredients, additives, cell types, pathogens, and like aspects, and ranges thereof, are for illustration only; they do not exclude other defined values or other values within defined ranges. The compositions, articles, and methods of the disclosure include those having any value or any combination of the values, specific values, more specific values, and preferred values described herein.

A leading substrate for liver cell culture and assay is, for example, Matrigel™ and Collagen I. Both are animal-derived and subject to lot-to-lot variability. Hepatocytes cultured on Matrigel, specifically formulated for hepatocytes, form spheroid aggregates and show enhanced function (see for example, Cyprotex publication library for general ADMETox information at www.cyprotex.com; Vanhaecke T., et al., Hepatocyte Cultures in Drug Metabolism and Toxicological Research and Testing, In *Cytochrome P450 Protocols*; Phillips, I. R., Shephard, E. A., Eds. Methods in Molecular Biology Series 320, Humana Press Inc., Totowa, N.J., 2006; pp. 209-227; LeCluyse, E. L., *European J. Pharin. Sci.* 2001, 13, 343-368). However, liver cells cultured on collagen are flat and spread, which is advantageous for proliferation, but not ideal for function. If the liver cells are sandwiched between two layers of collagen (termed a collagen sandwich), the cells adopt a polygonal appearance and show enhanced function.

Cellulose is a linear polymer of β-glucose linked together via β(1→4) glycosidic bonds. Structural modification of cellulose (see e.g., FIG. 1) allows for improved solubility and processability of the resulting material. Modified cellulose, such as hydroxyethyl cellulose, hydroxypropyl cellulose, methylcellulose or derivatives thereof, has been used (see www.herc.com/aqualon/aq_markets.html) as an associative thickener, emulsifier, and rheology modifier in a variety of industries including food, pharmaceutical, personal care and paint. In addition, Methocel™ (dow.com) films (or other hydroxymethyl, hydroxyethyl, and hydroxypropyl cellulose polymers) are known to be cell adhesion resistant materials and are used for anchorage independence assays (see for example, http://www.lbl.gov/lifesciences/BissellLab/labprotocols/anchorage.htm). The highly processed materials should have only limited variability.

Use of water soluble or swellable polymers suitable for cell culture can have several issues that should be considered, such as: 1) the water soluble polymers must be physically or chemically stabilized against, for example, water dissolution or water erosion during cell culture conditions; 2) molecular and formulation criteria can be useful in controlling surface characteristics; and 3) anchorage points for the polymers to the substrate surface may be needed, for example, for serum protein or cell attachment, and like modification and functionalization schemes. In embodiments of the disclosure, hydrophobe modified cellulose polymers can be transformed alone or further modified by compounding with a silica source or silica precursor or progenitor to address the aforementioned issues.

In embodiments, the disclosure provides hybrid materials and methods of use of the hybrid materials optionally including a silica source or silica precursor as a modifier for water soluble polymers, specifically, polysaccharides including, for example, hydrophobe modified hydroxyethyl cellulose or HMHEC, such as Natrosol and PolySurf, or like materials, and other water-soluble, cell compatible polymeric or coating materials. The silica precursors can serve several functions: 1) to stabilize the cellulose polymer or like water soluble or swellable polymer materials by providing crosslinking points, that is, the silica precursor when combined with the polymer component provides chemical cross-linking; 2) a wide variety of available silica precursors, such as silanes, can provide preparative and manufacturing flexibility in regulating surface characteristics including, for example, surface charge, surface affinity or compatibility, hydrophobicity, and modulus (e.g., through cross-linking); 3) surface properties can be adjusted by different methods of modification or functionalization through either the organic or inorganic portions of the hybrid material; and 4) to provide deposition points for serum proteins, and cell attachment. "Deposition points" or "anchoring points" are, for example, potential points for cellular protein attachment to the coating. A deposition point can be, for example, a charged group contained in a silane compounds, such as GAPS.

In embodiments, the disclosure provides cell culture coatings and coated substrates for cell culture comprised of the reaction product of an inorganic precursor component (e.g., silanes) and polymeric component such as a cellulose derivatized polymer (e.g., hydroxyethylcellulose), and optionally other water-soluble or water swellable polymers. For example, the inorganic and polymeric components can be combined in solution and applied to coat a supporting substrate, if desired. In addition to serving as anchoring points and as possible scaffolding structures within a softer hydrogel material, the inorganic component can serve as a crosslinker or cross-linking agent to further change the modulus of the hydrogel coating. The inorganic precursor component can be added, for example, during the coating process, as a post-treatment after casting of the film, or both.

Commonly owned and assigned copending U.S. Ser. No. 61/237,098 mentions methods of patterning hydrogels from cross-linkable polymers, such as polysaccharide-based polymers. The polymers can be photo-crosslinked without the use of photoinitiators, curable monomers, and harmful or toxic solvents or materials.

Commonly owned and assigned copending US20090227027 entitled "COATED CELL CULTURE," mentions a composition for use, for example, in cell culture surface modification and in cell culture articles. Also mentioned are methods of making the compositions and articles, and methods of using the compositions and articles.

In embodiments, the disclosed cell culture compositions and articles thereof, and the method of making and use provide one or more advantageous features or aspects, including for example as discussed below. Features or aspects recited in any of the claims are generally applicable to all facets of the invention. Any recited single or multiple feature or aspect in any one claim can be combined or permuted with any other recited feature or aspect in any other claim or claims.

In embodiments, the present disclosure provides a number of improvements and advantages, including, for example:

The starting components for the culture coating are commercially available, relatively inexpensive, and abundant.

The method of making the coating and article (i.e., the coating composition combined with a substrate) is versatile and can be used to mask various functional groups (e.g., charged, aromatic, and like molecular features) in the surface of the culture article.

The method of making the coating and article is versatile and can be used to make multiple formats that are ready-to-use.

The disclosed culture coating is non-toxic, and can be used as a drug delivery vehicle, for example, as an encapsulant for controlled drug release or controlled decay.

The disclosed culture coating has excellent processability because of its high initial water solubility, and is easy to handle and stored when transformed to the insoluble coating matrix.

The disclosed culture coating has excellent lot-to-lot consistency.

The disclosed culture coating and article are not at risk for contamination by adventitious agents.

The disclosed method of making the culture coating and article has excellent versatility in that a wide variety of commercially available silanes as a silica source material and a variety of water soluble polymers can be selected to provide a range of functional groups within the sol-gel or hydrogel matrix.

The disclosed culture article provides excellent controlled cell proliferation compared to tissue culture treated (TCT) culture media.

The disclosed cell culture coating and cell culture article can have excellent stability and can optionally be further processed, e.g., crosslinked using photochemical crosslinking, chemical crosslinking (e.g., sol-gel, esterification, etc.), and like transformation methods, or combinations thereof, to reduce the coating's water solubility and further enhance the coating's stability.

In embodiments, the present disclosure provides a cell culture surface coating comprising:

an hydrogel comprised of a water insoluble polymer comprised of a hydrophobe modified carbohydrate, an hydroxylated acrylate, or a combination thereof.

The coating can further include a silica source to, for example, form a sol-gel or to form an over coating layer. The water insoluble polymer can be, for example, a UV-ozone treated water soluble polymer comprised of a hydrophobe modified carbohydrate.

Figure 7:
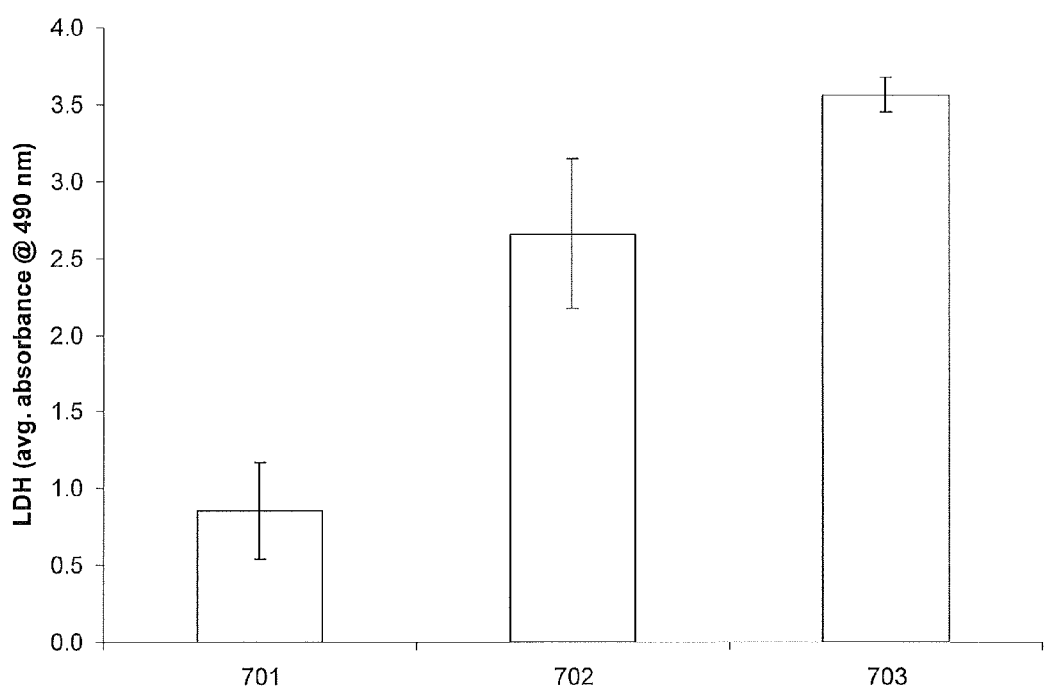
FIG. 7 shows an LDH assay on HepG2/C3A cells cultured on various silica/HMHEC hybrid films after 24 hours of culture.

The UV-ozone treated product of the combined silica source and water insoluble polymer cell culture surface coating has improved cell attachment and adhesion properties, such as shown in FIG. 7 compared to collagen-I control. The UV-ozone treatment can be accomplished with any suitable UV-ozone source. Other suitable or useful sources include, for example, an ozone generator source and a UV light source, and like ionizing radiation sources.

The water insoluble polymer can be, for example, a hydrophobe modified carbohydrate source selected, for example, from an hydroxalkyl cellulose, an hydrophobe modified cellulose, an hydrophobe modified hydroxyalkylcellulose, an hydrophobe modified alkylene oxide modified hydroxyalkylcellulose, or a combination thereof.

In embodiments, the hydrophobe modified carbohydrate or the hydroxylated acrylate can be, for example, substantially free of cross-linking monomers.

The hydroxylated acrylate, for example, a HEMA polymer, a HEMA copolymer, a HEMA-HEMA phosphate copolymer, or a combination thereof. The hydrophilic or hydroxylated acrylate polymer can be, for example, at least one hydroxyalkylacrylate monomer, or a combination thereof (e.g., HEMA monomers, and like monomers, including copolymers thereof).

The hydroxylated acrylate polymer can be, for example, an HEMA copolymer comprised of from about 10 to 90 mol % HEMA and from about 1 to about 10 mol % of HEMA-phosphate co-monomer, or a combination thereof.

The water insoluble polymer can be, for example, a UV-ozone-transformed water soluble polymer, a UV-ozone-transformed water swellable polymer, or a combination thereof.

The silica source can be, for example, a substituted and unsubstituted tetraalkyloxysilane (e.g., tetramethoxysilane), a substituted and unsubstituted alkyltrialkyloxysilane (e.g., methyl trimethoxysilane, gamma-aminopropyltrimethoxysilane), and like silane compounds or related compounds, or a combination thereof.

In embodiments, the coating can further comprise an overcoat layer comprised of a silica source component.

In embodiments, the coating can further comprise a container, for example, a vessel, a flask, a beaker, a microwell plate, a dish, a jar, and like form factors. The coating can further comprise a three dimensional disposition, for example, a 3D-scaffold, of the surface coating on a surface of the container.

In embodiments, the disclosure provides a method of making a cell culture article, comprising:
depositing a hydrophobe modified carbohydrate, an hydroxylated acrylate polymer, or a combination thereof on a substrate, and
contacting the deposited hydrophobe modified carbohydrate or acrylate polymer with an UV-ozone source.

The method of making can further comprise including a silica source with the hydrophobe modified carbohydrate, the hydroxylated acrylate, or a combination thereof.

In embodiments, the disclosure provides a method for cell culture comprising:

contacting cells and a cell culture article comprising:
at one least surface coating comprised of an hydrogel comprised of a water insoluble polymer comprised of a hydrophobe modified carbohydrate, an hydroxylated acrylate polymer, or a combination thereof, In embodiments, the water insoluble polymer component can be, for example, a hydrophobically modified cellulosic source, a hydrophilic or hydroxylated acrylate polymer, or a combination thereof, that has been exposed to a UV-ozone source. In embodiments, the water insoluble polymer component can be, for example, a sol-gel comprised of the polymer component and a silica source component, In embodiments, contacting of cells with a cell culture coated article can re-establish cell membrane polarity and increase cell function.

In embodiments the disclosure provides a coating composition for cell culture comprising:
a polymer matrix comprised of a hydrophobe modified polysaccharide comprising a polysaccharide having a plurality of hydrophobes. In embodiments the stability of the polymer matrix can be further improved by contacting the polymer matrix with, for example, a UV-ozone source to transform the matrix into a low or substantially water insoluble material.

In embodiments the disclosure provides a composition for cell culture comprising:
a cellulose-silica matrix comprised of a hydrophobe modified carbohydrate comprising a hydrophobe modified polysaccharide having a plurality of hydrophobes, and a silica source.

In embodiments the stability of the cellulose-silica matrix can be further improved by contacting the cellulose-silica matrix with, for example, a UV-ozone source to further transform the matrix into a low or substantially water insoluble material. In embodiments, the addition of a silica source to form a sol-gel improved the coating with respect to greater cell attachment, see FIG. 7 and accompanying discussion below.

In embodiments the disclosure provides a method for cell culture comprising:
providing a substrate coated with any of the abovementioned polymer matrices, such as a cellulose-silica matrix comprised of a hydrophobe modified polysaccharide and a silica source composition or like compositions, or a combination thereof;
contacting the coated substrate with a cell culture for a sufficient time to establish functional cells; and
harvesting the cells from the substrate.

In embodiments, the substrate can be, for example, comprised of a material selected from a metal oxide, a mixed metal oxide, a synthetic polymer, a natural polymer, and like materials, or combinations thereof.

In embodiments, the contacting of the coated substrate with a cell culture for a sufficient time to establish functional cells can be, for example, from about 3 to about 14 days for hepatocycle HepG2/C3A cells.

The cells of the cell culture can be, for example, any suitable primary cells, or associated immortalized cell lines, of any cell type such as hepatocytes. The cell culture can include, for example, cells actively producing albumin, antibodies, or like entities, and combinations thereof. The cells can be, for example, primary human hepatocytes (Fa2N4).

In embodiments the disclosure provides a method of making a cell culture article, comprising:
depositing a hydrophobe modified polysaccharide on a suitable substrate, and
exposing the deposited hydrophobe modified polysaccharide to an UV-ozone source or like source.

The resulting exposed surface can optionally be washed to remove any unreacted or residual water-soluble hydrophobe modified polysaccharide or like materials, or any low molecular weight water soluble products.

In embodiments, the method of making a cell culture article can further comprise including a silica source prior to depositing the hydrophobe modified polysaccharide on the substrate to form the cellulose-silica matrix. Alternatively or additionally, the silica source can be combined with the hydrophobe modified polysaccharide after the polysaccharide has been deposited on the substrate.

The depositing can be accomplished with, for example, any suitable coating method, such as simple pouring and evaporating, electrospinning, solution coating, slot coating, and like coating or film forming methods, or combinations thereof.

The hydrophobe can be, for example, a $C_{12-20}$ alkyl and the polysaccharide comprises a cellulose. The hydrophobe can be, for example, —O—; —S—R; —O—C(=O)R; —S—C(=O)R; —S—C(=S)R; —C(=O)R; —O—CH$_2$—CH(OH)—CH$_2$—O—R; —O—CH$_2$—CH(OH)—CH$_2$—O—C(=O)R; —O—CH$_2$—CH(OH)—CH$_2$—C(=O)R, and like groups, and combinations thereof, where R is a $C_{16-20}$ alkyl having a linear alkyl chain, a branched alkyl chain, or a mixture thereof, and the polysaccharide comprises a cellulose, an hydroxyalkyl cellulose, an oligomeric (hydroxyalkyl) cellulose, or mixtures thereof, the hydroxyalkyl celluloses having from 0 to about 3 hydroxyalkyl groups for each saccharide of the polysaccharide, the hydroxyalkyl group having from 2 to 6 carbon atoms. The polysaccharide can be, for example, a hydroxyethyl modified cellulose having from 0 to 3 hydroxyethyl groups for each glucose, the hydrophobe can be, for example, a —O—C(=O)R, where R is $C_{16-20}$ alkyl, and having a total hydroxyalkyl to hydrophobe mole ratio of from about 6:1 to about 1:1. The polysaccharide can be, for example, a hydroxyethyl modified cellulose having from 1 to 3 hydroxyethyl groups for each glucose, the hydrophobe can be a —O—C(=O)R, where R is $C_{18}$ alkyl, and having from about 2 to about 15 mole % hydrophobe and from about 85 to about 98 mole % polysaccharide. The coating can be, for example, from about 10 to about 90 wt % a hydrophobe modified cellulose; and from about 10 to about 90 wt % silica source. The hydrophobe modified cellulose can promote adhesion of the hydrogel to the substrate. The coatings or films of the composition can be, for example, optically clear.

The coating can further include additives, in lesser relative amounts of the base coating composition, for example, a biologically active compound comprising at least one of an amino acid, a peptide, a polypeptide, a protein, a carbohydrate, a lipid, a polysaccharide, a nucleic acid, a nucleotide, a polynucleotide, a glycoprotein, a lipoprotein, a glycolipid, a glycosaminoglycan, a proteoglycan, a growth factor, a differentiation factor, a hormone, a neurotransmitter, a pheromone, a chalcone, a prostaglandin, an immunoglobin, a monokine, a cytokine, an humectant, a fibrous protein, an adhesion compound, a de-adhesion compound, an enzyme, and like compounds, or a combination thereof.

In embodiments, the carbohydrate- or polysaccharide-based polymer can be, for example, a cellulose-based polymer such as hydroxyethylcellulose (HEC), hydroxypropylcellulose (HPC), methylcellulose (MC), hydroxyproplymethylcellulose (HPMC,) and like polymers, or combinations thereof. Vendors such as Sigma-Aldrich, Dow, and Aqualon offer a variety of cellulose polymers. For example, Sigma-Aldrich offers HEC having an average molecular weight of about 90 kDa, about 250 kDa, about 720 kDa, or about 1,300 kDa, Dow offers a variety of HEC products having 1% Brookfield Viscosities ranging from about 1100 to about 6000 cP and offers an HMHEC that is a hydrophobe modified HEC (CELLOSIZE HMHEC 500) having an HEC backbone with pendant hydrophobic groups, and Aqualon offers HEC as Natrosol 250 and HMHEC as PolySurf 67, having pendant cetyl groups. An hydrophobe modified cellulose or an hydrophobe-modified alkyleneoxide-modified hydroxyalkylcellulose can be, for example, an hydrophobe modified hydroxyethylcellulose (HMHEC), such as NATROSOL®PLUS CS, Grade 330.

The cross-linkable or ozone transformable polysaccharide-based polymer layer may be disposed on any suitable substrate. The substrate may vary depending on the particular use of the cell culture article on which the matrix is coated. Examples of suitable substrates include ceramic substrates, glass substrates, plastic or other polymeric substrates, or combinations thereof. In embodiments, the substrate can be a glass material such as soda-lime glass, Pyrex® glass, Vycor® glass, quartz glass; silicon. In embodiments, the substrate can be a plastic or polymers including dendritic polymers, such as poly(vinyl chloride), poly(vinyl alcohol), poly(methyl methacrylate), poly(vinyl acetate-co-maleic anhydride), poly(dimethylsiloxane)monomethacrylate, cyclic olefin polymers, fluorocarbon polymers, polystyrenes, polypropylene, polyethyleneimine; copolymers such as poly(vinyl acetate-co-maleic anhydride), poly(styrene-co-maleic anhydride), poly(ethylene-co-acrylic acid), and like polymers, or combinations thereof.

Any article using the disclosed matrix compositions can be coated in accordance with the teachings presented herein or any other suitable coating method. In embodiments, the cell culture article can include a cellulose-silica matrix layer as described herein. Examples of cell culture articles to which a cellulose-silica matrix layer can be applied include single and multi-well plates, such as 6, 12, 96, 384, and 1536-well plates, jars, petri dishes, flasks, multi-layered flasks, beakers, plates, roller bottles, slides, such as chambered and multi-chambered culture slides, tubes, cover slips, bags, membranes, hollow fibers, beads and microcarriers, cups, spinner bottles, perfusion chambers, bioreactors, CellSTACK®, fermenters, and like articles, or combinations thereof.

The hydrophobe modified poly-glucose polymer can be, for example, an hydrophobe modified cellulose-based polymer, an hydrophobe modified dextran polymer, an hydrophobe modified amylase polymer, and like hydrophobe modified polymers. The polysaccharide-based polymer can be, for example, hydroxypropylcellulose, methylcellulose, hydroxyproplymethylcellulose, hydroxyethylcellulose, amylose, dextran, xylan, and like polymers, or combinations thereof.

In embodiments the substrate can be, for example, plastic, the hydrophobe modified polysaccharide can be a partially cetyl substituted alkylated hydroxyethylcellulose, or like hydrophobe and cellulose modifications, or combinations.

In embodiments, the coated substrate can be used in biosensor applications, such as label-free or label-independent detection having an resonant waveguide grating, or like biosensing applications.

HEC functional group modification. Additionally or alternatively, polysaccharides of the disclosure can be further functionally modified with, for example, urethanes, maleimides, esters, functionalized with biological macromolecules, or like groups for increasing or decreasing specific intra- or interchain interactions of hydrophobically modified groups.

The hydroxyl groups of carbohydrate can be partially or fully reacted with various reagents to afford derivatives with useful cell culture coating properties. Cellulose esters and cellulose ethers are examples of readily available commercial materials. Lower molecular weight modified cellulose esters are known, such as cellulose acetate and cellulose triacetate, which are known film- and fiber-forming materials having various industrial uses. Ether modified cellulose derivatives can be selected as the hydrophobe modified polysaccharide or used as starting material for further hydrophobic derivatization and can include, for example, alkycellulose, such as incompletely alkylated methyl or ethyl cellulose. Other suitable cellulose starting materials can include, for example, hydroxypropyl cellulose, carboxymethyl cellulose, hydroxypropyl methyl cellulose, hydroxyethyl methyl cellulose, and like materials, or combinations thereof.

HMHEC alkyl ethers, hydroxy alkyl ethers, esters, and like hydrophobically linked HECs are commercially available or can be readily prepared using various reactants, see for example, the working examples and above mentioned chemical structures in FIG. 1. If desired one can append biologic molecules of interest such as peptides, growth factors (such as HGF), antioxidants, glycans, or like molecules to the hydrophobe modified polysaccharides to further modify substrate coating surface properties, such as substrate adhesion, cellular attachment, cell function, cell proliferation, and cell release properties. The polysaccharide polymer can be further modified using, for example, standard carbohydrate and polymer functionalization techniques to attach a variety of macromolecules. For example, one can incorporate a maleimide functional group using a Mitsunobu reaction ($PPh_3$, diethyl azodicarboxylate as catalyst) to easily and selectively attach a thiol-containing molecule, such as cysteine modified polypeptide, to the polymer. Alternatively, any thiol containing compound can be used to add another functional group of interest if a spacer is desired or necessary for proper ligand display.

The abundance of hydroxy groups in the HMHEC allows for polymer modification using ester formation using, for example, coupling reagent combination such as EDC/NHS (N-(3-Dimethylaminopropyl)-N'-ethylcarbodiimide and N-hydroxysulfosuccinimide), or like carbodiimide coupling reagents. A preactived carboxylic acid such as a succinimide ester or p-nitrophenol carbonate ester can also be used in the absence of the coupling reagents.

Any of the aforementioned or like chemistries can also be used to further modify the polymer with hydrophobe groups. This modification can increase the hydrophobic interaction(s) between the polysaccharide chains and permit control of useful cell culture. Other self-associating groups, such as perfluoroalkyl or silicone, can be incorporated into the coating formulation to provide additional coating cohesion, but not cell adhesion, particularly if there is an interest in probing specific ligand-receptor interactions.

Alternative or additional polymers Other suitable water soluble starting polymers can include, for example, poly(vinyl alcohol), poly(acrylic acid), and linear or branched polysaccharides including, for example, dextran, agarose, chitosan, amylose, amylopectin, and like polymers, or combinations thereof can be selected as additives or can be chemically modified with hydrophobic or like associating groups, including self-complexing and complementary binding pairs, to produce, for example, viscoelastic coatings having hydrogel-like properties that are suitable for cell culture and assay. Further adjustment of the coating properties with respect to, for example, the cell type, and assay, can be accomplished by, for example, combining one or more of the coating examples mentioned above or disclosed herein.

The disclosure provides, in embodiments, hydrophobe modified polysaccharides, including certain modified celluloses, as a material for cell culture that provides in vivo-like conditions that can enhance cellular function. The substrate coatings can include hydrophobe modified polysaccharides, or other polymers such as poly(vinyl alcohol) that are initially water soluble and modified with hydrophobe groups that can provide additional cohesive non-covalent crosslinking interactions.

In embodiments, the disclosure provides a hydrophobe derivatized polysaccharide for cell culture substrate coating for anchorage-dependent, such as Natrosol® and other HMHEC coated substrates. The hydrophobe derived polysaccharide can be used as-is, for example, to produce thin film surfaces to culture cells, as a gel to encapsulate cells or cell clusters, or like applications. The film can be strengthened by reinforcing the existing hydrophobic interactions present between the polymer chains. With further chemical functionalization, biologically relevant macromolecules or ligands can be attached. In embodiments the polymer can be crosslinked and made into 3-dimensional scaffolds.

In embodiments, various biocompatible polymer materials can additionally be used in combination or in admixture with the hydrophobe modified carbohydrate or hydroxylated polymer compounds and compositions of the disclosure, and can include, for example, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes, and copolymers thereof, nitro celluloses, polymers of acrylic and methacrylic esters, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methylmethacrylate), poly(ethylmethacrylate), poly(butylmethacrylate), poly(isobutylmethacrylate), poly(hexylmethacrylate), poly(isodecylmethacrylate), poly (laurylmethacrylate), poly(phenylmethacrylate), poly (methacrylate), poly(isopropacrylate), poly(isobutacrylate), poly(octadecacrylate), polyethylene, polypropylene, poly (ethylene glycol), poly(ethylene oxide), poly(ethylene terephthalate), poly(vinyl alcohols), poly(vinyl acetate), poly (vinyl chloride), polystyrene, polyhyaluronic acids, casein, gelatin, gluten, polyanhydrides, polyacrylic acid, alginate, chitosan, and any copolymers thereof, or any combination thereof.

Figure 1B:
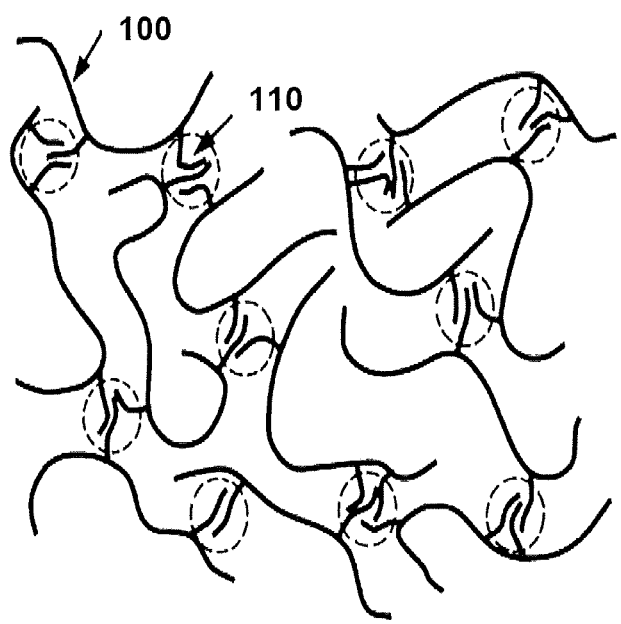

Referring to the Figures, FIGS. 1A and 1B, respectively, show typical structures of HECs such as a hydrophobe modified hydroxyethylcellulose (HMHEC) modified via stearyl ethers (1A), and interchain noncovalent crosslinking (circled) of these hydrophobe modified hydroxyethylcellulose (HMHEC) polymers in aqueous solution (1B) that are believed to result in gel formation in solution via hydrophobic interactions between the hydrophobe alkyl side chains (110) of the polysaccharide (100) or like functionalized polymer (100).

Figure 2:
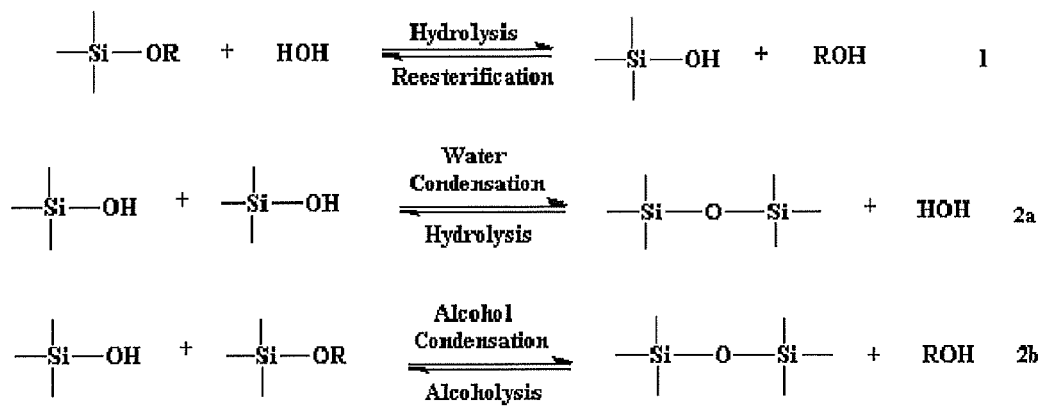
FIG. 2 shows typical reactions in the sol-gel process: hydrolysis (eq. 1), water condensation (eq. 2a) and alcohol condensation (eq. 2b).
Figure 3:
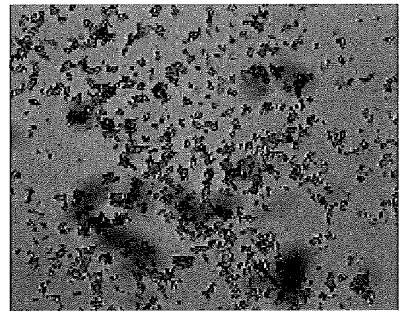
FIGS. 3A to 3D show HepG2/C3A cells after 24 hours of culture on HEC/TMOS (3A), PS67/TMOS (3B), HEC/MTMS (3C), and collagen control (3D).
Figure 3:
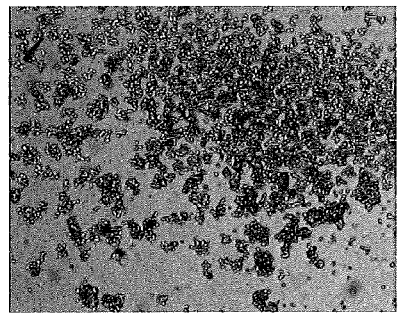
Figure 3:
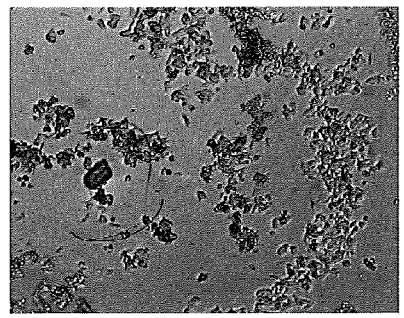
Figure 3:
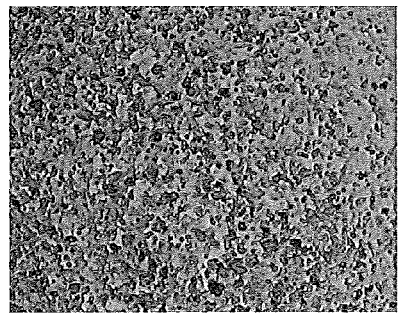
Figure 4:
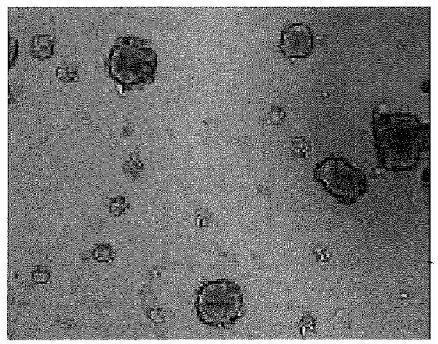
FIGS. 4A to 4D show images of HepG2/C3A cells after 7 days of culture on HEC/TMOS (4A), PS67/TMOS (4B), HEC/MTMS (4C), and collagen control (4D).
Figure 4:
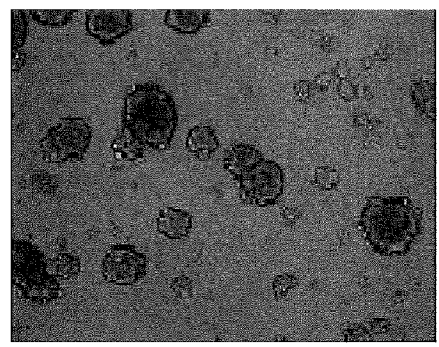
Figure 4:
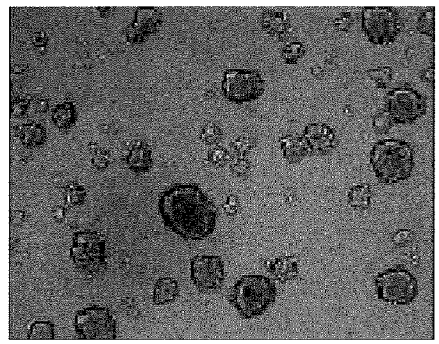
Figure 4:
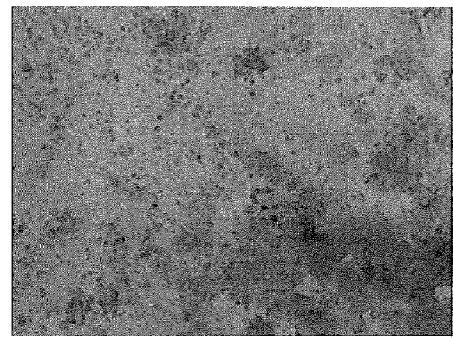

FIG. 2 shows typical reactions in the sol-gel process: silane hydrolysis (eq. 1), water condensation with siloxane bond formation (eq. 2a), and alcohol condensation with siloxane bond formation (eq. 2b). The condensation reactions can couple the silica precursor to the cellulose polymer.

FIGS. 3A to 3D show HepG2/C3A cells after 24 hours of culture on HEC/TMOS (3A), PS67/TMOS (3B), HEC/MTMS (3C), and a collagen-I (3D) as a comparative control. Cells on the disclosed cellulose/silica hybrid surfaces can form clusters or spheroids that were attached to the substrate. In contrast, on collagen the cells were flat and spread out and had a two-dimensional morphology. Coating composition samples 3A and 3C were irradiated with a UV-ozone source, whereas coating sample 3B was not irradiated with the UV-ozone source.

FIGS. 4A to 4D show HepG2/C3A cells after 7 days of culture on HEC/TMOS (4A), PS67/TMOS (4B), HEC/MTMS (4C), and collagen-I control (4D). Cells on the disclosed cellulose/silica hybrid surfaces form clusters or spheroids that are attached to the substrate. In contrast, on collagen the cells are flat and spread out and had a two-dimensional morphology which is indicative of an improved basal level for the disclosed surface coating composition. Coating composition samples 4A and 4C were exposed in ambient air with a UV-ozone source, whereas coating sample 4B was not exposed to the UV-ozone source.

Figure 5A:
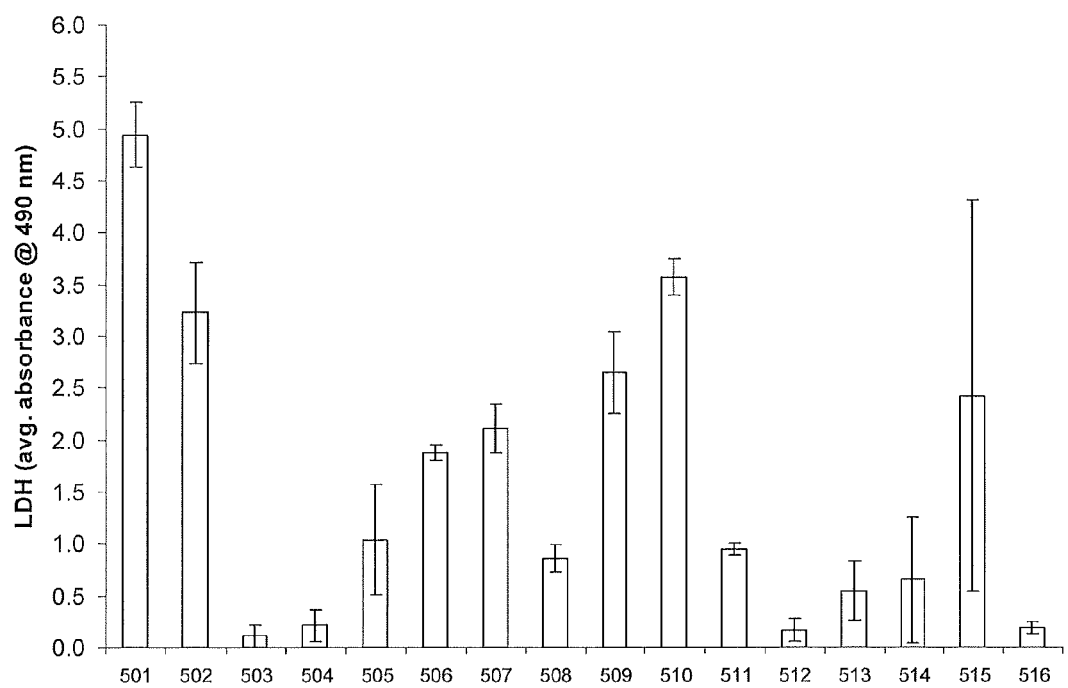
FIGS. 5A to 5B show bar charts of a Promega MTS assay on HepG2/C3A (5A) and Fa2N-4 (5B) cells cultured on various silica/HMHEC hybrid films after 24 hours of culture.
Figure 5B:
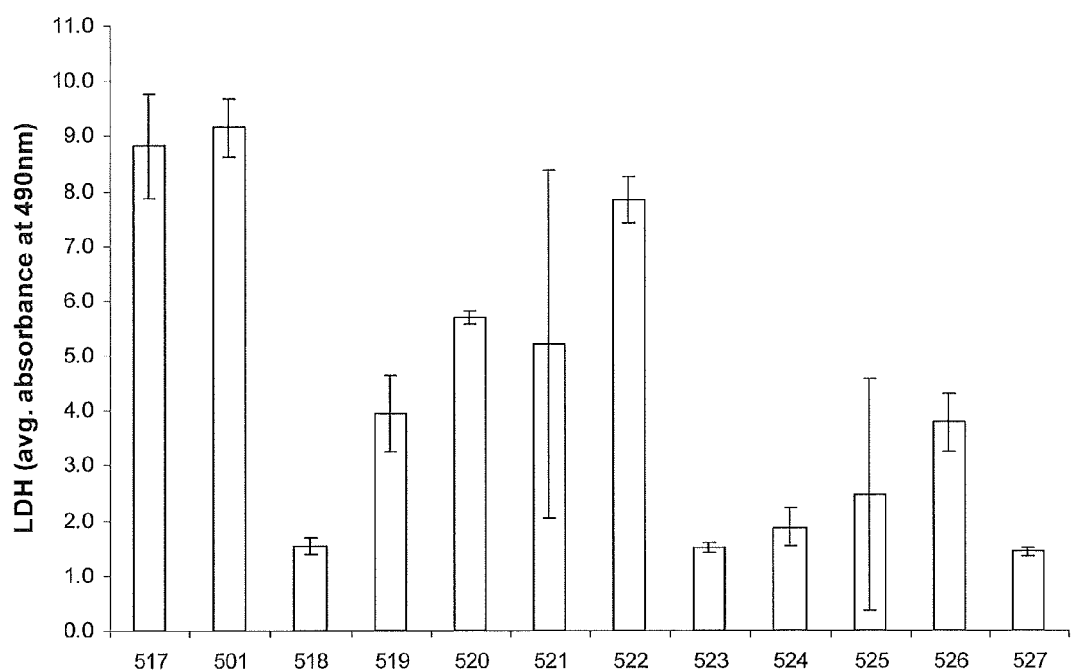
Figure 6A:
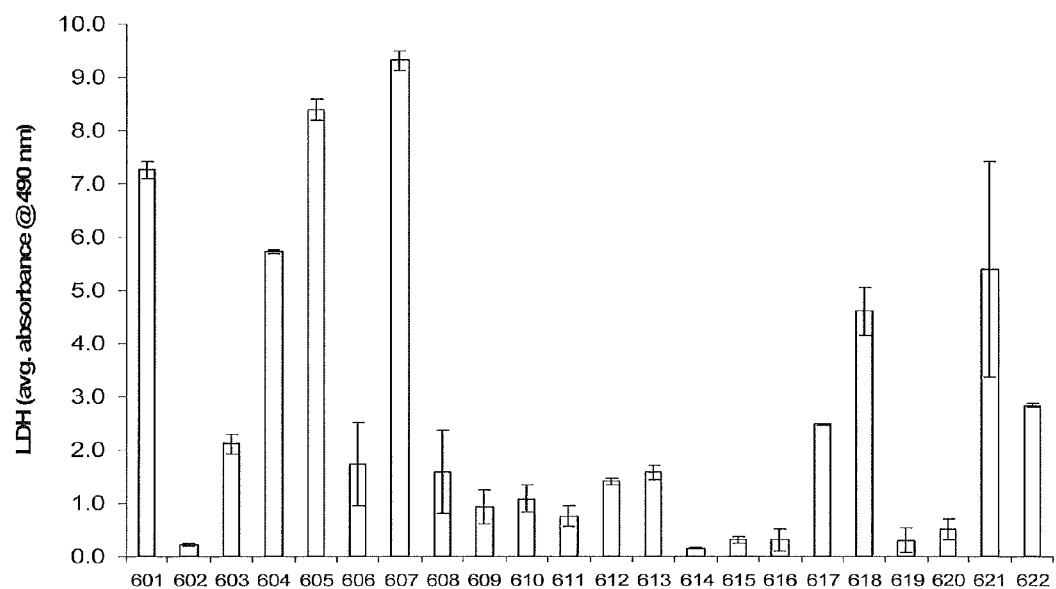
FIGS. 6A and 6B show bar charts of a Promega MTS assay on HepG2/C3A (6A) and Fa2N-4 (6B) cells cultured on various silica/HMHEC hybrid films after 24 hours of culture.
Figure 6B:
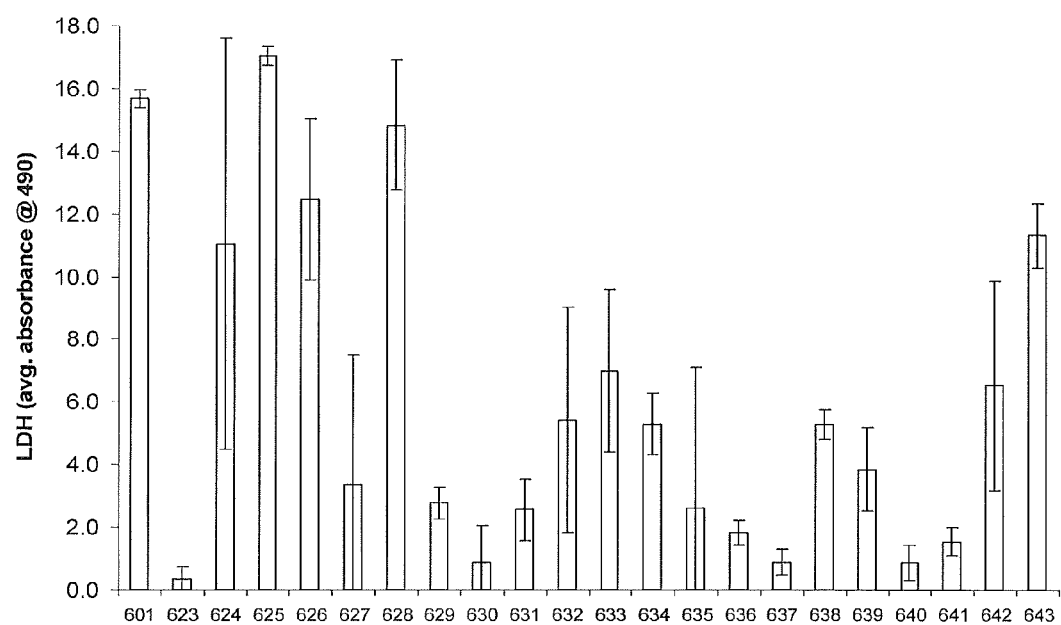

FIGS. 5A to 5C show bar charts of a Promega MTS assay results of HepG2/C3A (5A) cells and Fa2N-4 (5B) cells that were cultured on various disclosed silica/HMHEC hybrid thin (e.g., 1 to 100 microns) films after 24 hours of culture as measured by a standard LDH lysis assay. Cells cultured simultaneously on collagen coated polystyrene were used as a control. The results show that HepG2/C3A cells attach to the silica/HMHEC hybrid coatings and proliferate at a moderate rate (slower than cells on TCT, but approaching about 75% of collagen) which is advantageous for function, such as gene expression, albumin secretion, and Cytochrome P450 family activity (e.g., C1A2/2P6/3A). Increasing silica content in the surface coating can lead to an increase in cell number. HepG2/C3A cell attachment can increase with increasing UV exposure time (see 5A: 503 to 507), and with increasing silica (TMOS) content (see 5A: 508, 509, and 510). Fa2N-4 cells also show increased attachment with increasing silica source (TMOS) content (see 5B: 518, 519, and 520). In FIG. 5A: 501 is a collagen type-I control; 502 is Matrigel™; 503 is PS67 crosslinked by UV treatment for 1.5 minutes; 504 is PS67 crosslinked by UV-ozone treatment for 2 minutes; 505 is PS67 crosslinked by UV treatment for 2.5 minutes; 506 is PS67 crosslinked by UV-ozone treatment for 3 minutes; 507 is PS67 crosslinked by UV-ozone treatment for 5 minutes; 508 is HEC/TMOS-1:2 (w:v); 509 is HEC/TMOS-1:4 (w:v); 510 is HEC/TMOS-1:6 (w:v); 511 is HEC/TMOS/GAPS-10:20:1 (w:v:v) crosslinked by UV-ozone treatment for 10 minutes; 512 is PS67/TMOS-2:1 (w:v) with no UV-ozone treatment; 513 is PS67/TMOS-5:1 (w:v) with no UV-ozone treatment; 514 is PS67/MTMS-5:1 (w:v) with no UV-ozone treatment; 515 is HEC/MTMS-1:4 (w:v) crosslinked by UV-ozone treatment for 10 minutes; and 516 is PS67/MTMS-5:1 (w:v) crosslinked by UV-ozone treatment for 10 minutes. In FIG. 5B: 501 is collagen type-I control; 517 is collagen, type-I plated with 5% fetal bovine serum; 518 is HEC/TMOS-1:2 (w:v) crosslinked by UV-ozone treatment for 10 minutes; 519 is HEC/TMOS-1:4 (w:v) crosslinked by UV-ozone treatment for 10 minutes; 520 is HEC/TMOS-1:6 (w:v) crosslinked by UV-ozone treatment for 10 minutes; 521 is HEC/TMOS/GAPS-10:20:1 (w:v:v), crosslinked by UV-ozone treatment for 10 minutes; 522 is Tissue Culture Treated (TCT) polystyrene control; 523 is PS67/TMOS-2:1 (w:v) with no UV-ozone treatment; 524 is PS67/TMOS-5:1 (w:v) with no UV-ozone treatment; 525 is PS67/MTMS-5:1 (w:v) with no UV-ozone treatment; 526 is HEC/MTMS-1:4 (w:v), crosslinked by UV-ozone treatment for 10 minutes; and 527 is PS67/MTMS-5:1 (w:v), crosslinked by UV-ozone treatment for 10 minutes FIGS. 6A and 6B show charts of a LDH lysis metabolic assay results from HepG2/C3A (6A) cells and Fa2N-4 (6B) cells cultured on exemplary silica/HMHEC hybrid thin films after 24 hours of culture. Cells were cultured simultaneously on collagen coated polystyrene as controls. Chemical modification (GAPS post treatment) of the surface improves the 24 hour cell attachment, see FIG. 6A samples 607, 621, and 622, and FIG. 6B samples 628, 642, and 643. Several samples approach or exceed a target attachment value of about 75% compared to collagen.

In FIG. 6A: 601 is collagen type-I control; 602 is HEC/TMOS-1:2 (w:v) crosslinked by UV-ozone treatment for 10 minutes; 603 is HEC/TMOS-1:4 (w:v) crosslinked by UV-ozone treatment for 10 minutes; 604 is HEC/TMOS-1:5 (w:v) crosslinked by UV-ozone treatment for 10 minutes; 605 is HEC/TMOS-1:6 (w:v) crosslinked by UV-ozone treatment for 10 minutes; 606 is HEC/TMOS/GAPS-10:20:1 (w:v:v) crosslinked by UV-ozone treatment for 10 minutes; 607 is HEC/TMOS-1:1 (w:v) crosslinked by UV-ozone treatment for 10 minutes, and 2% GAPS post treatment; 608 is PS67 crosslinked by UV-ozone treatment for 10 minutes; 609 is PS67 crosslinked by UV-ozone treatment for 5 minutes; 610 is PS67 crosslinked by UV-ozone treatment for 20 minutes; 611 is PS67/TMOS-2:1 (w:v) crosslinked by UV-ozone treatment for 20 minutes; 612 is PS67/TMOS-5:1 (w:v) crosslinked by UV-ozone treatment for 10 minutes; 613 is PS67/MTMS-5:1 (w:v) crosslinked by UV-ozone treatment for 10 minutes; 614 is PS67/TMOS-1:1 (w:v) with no UV-ozone treatment; 615 is PS67/TMOS-2:1 (w:v) with no UV-ozone treatment; 616 is PS67/TMOS-5:1 (w:v) with no UV treatment; 617 is PS67/MTMS-5:1 (w:v) with no UV treatment; 618 is PS67 with no UV-ozone treatment; 619 is PS67/TMOS/GAPS-10:10:1 (w:v:v); 620 is PS67/TMOS/GAPS-20:20:1 (w:v:v); 621 is PS67/TMOS-1:1 (w:v) and 2% GAPS post treatment; and 622 is PS67/TMOS-1:2 (w:v) and 2% GAPS post treatment.

In FIG. 6B: 601 is collagen type-I control; 623 is HEC/TMOS-1:2 (w:v) crosslinked by UV-ozone treatment for 10 minutes; 624 is HEC/TMOS-1:4 (w:v) crosslinked by UV-ozone treatment for 10 minutes; 625 (same as 604) is HEC/TMOS-1:5 (w:v) crosslinked by UV-ozone treatment for 10 minutes; 626 (same as 605) is HEC/TMOS-1:6 (w:v) crosslinked by UV-ozone treatment for 10 minutes; 627 is HEC/TMOS/GAPS-10:20:1 (w:v:v) crosslinked by UV-ozone treatment for 10 minutes; 628 (same as 607) is HEC/TMOS-1:1 (w:v) crosslinked by UV-ozone treatment for 10 minutes and 2% GAPS post treatment; 629 is PS67 crosslinked by UV-ozone treatment for 10 minutes; 630 is PS67 crosslinked by UV-ozone treatment for 5 minutes; 631 is PS67 crosslinked by UV-ozone treatment for 20 minutes; 632 is PS67/TMOS-2:1 (w:v) crosslinked by UV-ozone treatment for 20 minutes; 633 is PS67/TMOS-5:1 (w:v) crosslinked by UV-ozone treatment for 10 minutes; 634 is PS67/MTMS-5:1 (w:v) crosslinked by UV-ozone treatment for 10 minutes; 635 is PS67/TMOS-1:1 (w:v) with no UV-ozone treatment; 636 is PS67/TMOS-2:1 (w:v) with no UV-ozone treatment; 637 is PS67/TMOS-5:1 (w:v) with no UV-ozone treatment; 638 is PS67/MTMS-5:1 (w:v), no with UV-ozone treatment; 639 is PS67 with no UV-ozone treatment; 640 is PS67/TMOS/GAPS-10:10:1 (w:v:v); 641 is PS67/TMOS/GAPS 20:20:1 (w:v:v); 642 is PS67/TMOS-1:1 (w:v) with 2% GAPS post treatment; and 643 is PS67/TMOS-1:2 (w:v) with 2% GAPS post treatment.

FIG. 7 shows an LDH assay on HepG2/C3A cells cultured on various silica/HMHEC hybrid thin films after 24 hours of culture. The results show an increase in cell attachment with increasing silica content. In FIG. 7: 701 is HEC/TMOS-1:2 (w:v); 702 is HEC/TMOS-1:4 (w:v); and 703 is HEC/TMOS-1:6 (w:v).

FIGS. 8A to 8C show HepG2/C3A cells after 24 hours of culture on some examples of tetramethoxysilane/HMHEC hybrid film coatings. Cell attachment increased as TMOS concentration increased (8A=2×, 8B=4×, 8C=6×TMOS).

Figure 9:
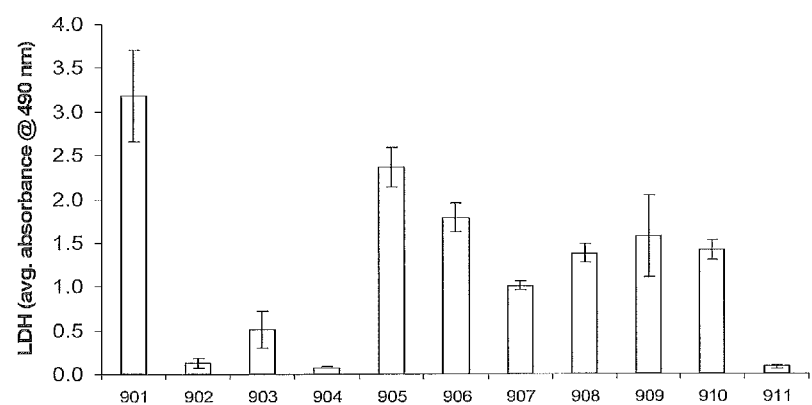
FIG. 9 shows a chart of an LDH assay of primary hepatocytes cultured on various silica/HEMA hybrid films after 24 hours of culture.

FIG. 9 shows a chart of an LDH assay of primary hepatocytes cultured on various silica/HEMA/HEMA-phosphate hybrid thin films after 24 hours of culture. The results show an increase in cell attachment with silica content. Examples including 5P and 10 P containing 5 wt % and 10 wt %, respectively, of a negatively charged phosphate group monomer, i.e., a HEMA copolymer having 95 wt % HEMA and 5 wt % phosphate modified HEMA, and a HEMA copolymer having 90 wt % HEMA monomer and 10 wt % phosphate modified HEMA monomer. In FIG. 9: 901 is collagen type-I control; 902 is 5P; 903 is 5P/10P-1:1 (w:w); 904 is 10P; 905 is 5P/TMOS-5:1 (w:v); 906 is 5P/10P/TMOS-5:5:2 (w:w:v); 907 is 10P/TMOS-5:1 (w:v); 908 is 5P/TMOS-1:1 (w:v); 909 is 5P/10P/TMOS-1:1:2 (w:w:v); 910 is 10P/TMOS-1:1 (w:v); and 911 is HEMA/TMOS-1:1 (w:v).

EXAMPLES

The following examples serve to more fully describe the manner of using the disclosure, and to further illustrate and demonstrate specific examples of best modes contemplated for carrying out various aspects of the disclosure. These examples do not limit the scope of the disclosure, but rather are presented for illustrative purposes.

General procedure for Silica/Carbohydrate film coating The water soluble polymer, water swellable polymer, or both a water soluble and water swellable polymer, such as hydroxyethylmethacrylate (co)polymers, hydroxyethylcellulose (HEC), or derivatives thereof, was or were dissolved in deionized water or another appropriate solvent or solvent mixture. Silica precursors (i.e., silica source component) were added, and the resulting mixture was coated on any appropriate cell culture vessels including, for example, flasks, petri dishes, well plates, slides, and like surfaces. Standard coating methods such as drop casting, dip coating, spin coating, and like methods can be used to apply a film to the substrate surface. Coatings were allowed to dry, either under ambient conditions or by heating. Upon drying, the coatings are stable under ambient conditions and can be sterilized using typical sterilization techniques, such as ethanol wash, and UV or gamma irradiation.

Cells (HepG2/C3A) cultured on silica/HMHEC hybrids form multicellular aggregates (spheroid-like, see for example, FIGS. 3 and 4) with similar morphology to those cultured on other soft, hydrophilic coatings such as Matrigel. For example, cell attachment on silica/HEC hybrid (sol-gel composition) was greater than attachment on HEC alone. Also, cell proliferation on the disclosed substrates is low compared to cells cultured on TCT, which is consistent with cells with more in vivo-like function (see FIGS. 5 and 6).

General cell culture procedure HepG2/C3A cells (ATCC No. CRL-10741) were cultured in Eagle's Minimum Essential Medium (ATCC No. 30-2003) supplemented with 10% Fetal Bovine Serum (Invitrogen No. 16000-077) and 1% Penicillin-Streptomycin (Invitrogen No. 15140-155). Cells were incubated at 37° C., in 5% $CO_2$ and 95% relative humidity.

Cells were seeded on the modified cellulose coatings of the disclosure at 5,000 cells in 100 microL media per well in 96-well microplate format. Media was replaced daily. Media aliquots were taken at assigned intervals to be assayed for albumin production. Albumin levels were determined using Micro-Albumin Quantitative Test (Biomeda No. EU-1057). CellTiter96® Aqueous One Solution MTS assay (Promega No. G3581) was used for quantifying cell number.

Cryo-preserved primary human hepatocytes were thawed and purified according to standard procedures. In 96-well plate format, primary cells were seeded at 50 to 60K cells per well in 100 microL MFE plating media (supplemented with 10% fetal bovine serum). The cells were incubated overnight at standard culture conditions (37° C., 5% $CO_2$, 95% relative humidity) to allow for optimal attachment. Media was then replaced with serum free maintenance MFE media.

Lysis LDH assays were performed as a marker of remaining live cells.

Figure 8:
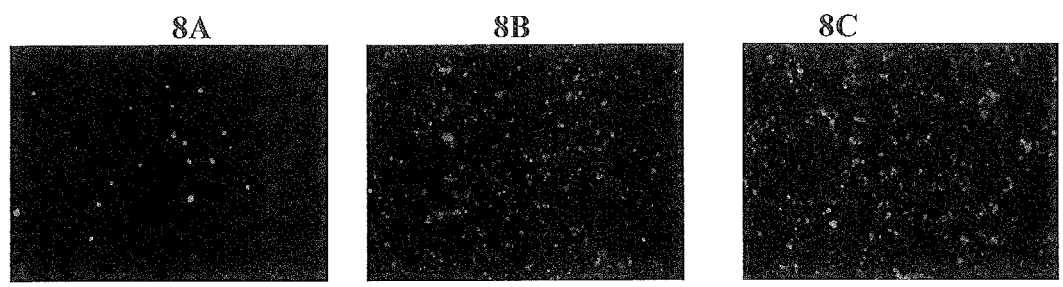
FIGS. 8A to 8C show HepG2/C3A cells after 24 hours of culture on some examples of tetramethoxysilane/HMHEC hybrid film coatings.

General procedure for post-treated silica/hydrophobe modified carbohydrate or acrylate polymer film coatings The water soluble/swellable polymer, such as hydroxyethyl methacrylate (co)polymers, hydroxyethylcellulose or derivatives thereof, was coated using any of the coating methods mentioned in the above general coating procedure. Upon drying the coated film, an aqueous silane solution was added to the coated cell culture vessel and allowed to react. After rinsing and drying (at ambient temperatures or with heating), the coatings were stable under ambient conditions. Cell attachment on these materials increased with increasing silica content (FIGS. 7 and 8).

UV-ozone transformation The cross-linkable polysaccharide-based polymer layer can be exposed to any suitable amount of UV light using a UV-ozone source to promote cross-linking or like decreased water solubility and increased viscosity transformations. The intensity of the UV-ozone source or time of exposure can be varied to achieve a desired amount of cross-linking. In embodiments, a cross-linkable polysaccharide-based polymer layer can be exposed to, for example, about 50 and about 300 $mJ/cm^2$ UV radiation, for example, from about 1 minute and about 20 minutes, in ambient air.

The silica source is not necessary to achieve suitable "crosslinking" or insolubility transformation effect. The UV-ozone source irradiated polymer can transformation in the absence of the silica source. The combination of the polymer and silica source produces a sol-gel product that visually appears to be physically unchanged upon UV-ozone exposure. However, a difference in cell response, such as improved cell attachment and improved cell adhesion to the coated substrate, can be measured for an UV-ozone irradiated sol-gel product compared to an un-irradiated sol-gel product, see FIG. 7.

The UV-ozone treatment of the water soluble polymer or the combination of the water soluble polymer with a silica source can lead to water insoluble hydrogel products. UV-ozone treatment, silica source addition, or both, leads to products that have improved cell adhesion. The combination of UV-ozone treatment and silica source addition steps can provide further enhanced performance, such as improved cell attachment and improved cell adhesion to the coated substrate.

Example 1

Substrate film casting procedure—HEC and TMOS coating HEC (1.25 g) was completely dissolved in deionized water (250 mL) and stirred vigorously for about 2 hours to provide a 0.5 wt % solution. Then 1.25 mL tetramethylorthosilicate (TMOS) was added to the HEC solution with stirring to provide a 1:1 (w:v) HEC/silica solution. After approximately 10 minutes, the combined HEC/silica solution was added to a well plate (e.g., 100 microL per well in a 96 well plate; 0.5 mL per well, 24 well plate; 1 mL per well, 12 well plate; 2 mL per well, 6 well plate). The solution was allowed to evaporate at room temperature 16 hours with lid on, followed by 75° C. for 8 hours, until dry. The plates were sterilized by UV irradiation (1 hr @ 366 nm).

Example 2

Substrate film casting procedure—HEC and TMOS, TEOS, and MTMS coating HEC (1.25 g) was completely dissolved in deionized water (250 mL) and stirred vigorously for about 16 hours to provide a 0.5 wt % solution. Then 0.5 mL tetramethylorthosilicate (TMOS), methyltrimethoxysilane (MTMS), and tetraethylorthosilicate (TEOS) were added to the 50 g batches of the HEC solution with stirring to provide a 1:2 (w:v) HEC/silica solution. After approximately 10 minutes, the combined HEC/silica solution was added to a well plate as above (e.g., 100 microL per well in a 96 well plate). The solution was allowed to evaporate at room temperature 16 hours with lid on, followed by 75° C. for 8 hours, until dry. The plates were sterilized by UV irradiation (1 hr @ 366 nm).

Example 3

Substrate film casting procedure—HEC and TEOS variation HEC (1.25 g) was completely dissolved in deionized water (250 mL) and stirred vigorously for about 16 hours to provide a 0.5 wt % solution. Then varying amounts of tetramethylorthosilicate (TMOS) were added to 50 g batches of the HEC solution with stirring according to the tabulated schedule:

| TMOS (mL) | HEC:silica (w:v) |
|---|---|
| 0.25 mL | 1:1 |
| 0.50 mL | 1:2 |
| 1.0 mL | 1:4 |
| 1.5 mL | 1:6 |
| 2.5 mL | 1:10 |

After approximately 10 minutes, the combined HEC/silica solutions were added to well plates as above. The solution was allowed to evaporate at room temperature 16 hours with lid on, followed by 75° C. for 8 hours, until dry. The plates were sterilized by UV irradiation (1 hr @ 366 nm).

Example 4

Substrate film casting procedure—HEC and TEOS and GAPS HEC (1.25 g) was completely dissolved in deionized water (250 mL) and stirred vigorously for about 16 hours to provide a 0.5 wt % solution. Then 0.875 mL tetramethylorthosilicate (TMOS) and 0.125 mL γ-aminopropyltriethoxysilane (GAPS) were added to the 50 g of the HEC solution with stirring to provide a 1:3.5:0.5 (w:v:v) HEC/TMOS/GAPS solution. After approximately 10 minutes, the combined HEC/silica solution was added to a well plate as above. The solution was allowed to evaporate at room temperature 16 hours with lid on, followed by 75° C. for 8 hours, until dry. The plates were sterilized by UV irradiation (1 hr @ 366 nm).

Example 5

UV-ozone transformation of water-soluble polymer to water insoluble film polymer coating A solution of PolySurf 67 was allowed to evaporate to dryness (60° C.) and was exposed to a UV-ozone light source (wavelengths 185/254 nm) for 10 minutes in ambient air and temperature and situated at about 1.5 inches from the coating. There was no apparent change in the film after UV-ozone irradiation. The only apparent visual change was noticed upon addition of water or if the films were exposed to areas of high humidity. When water was added the UV-ozone transformed polymer coating swelled slightly but did not dissolve.

Example 6

HEMA/silica film coatings Hydroxyethylmethacrylate (co)polymers and like polymers can also be used in place of hydroxyethyl cellulose (HEC). Hydroxyethyl-methacrylate (HEMA) was dissolved in ethanol (1 wt %) by stirring 16 hrs at room temperature. To separate 50 g portions of the HEMA solution, TMOS in amounts of 0.25 mL (1:1, w:v), 0.50 mL (1:2, w:v), or 1.25 mL (1:5, w:v) was separately added with stirring. After approximately 10 minutes, the combined HEMA/silica solutions were added to individual well plates as above. The covered (lid on) solution was allowed to evaporate 16 hrs at room temperature, followed by 60° C. for 8 hours, until dry. The plates were sterilized by UV irradiation (1 hr @ 366 nm). Cell attachment (primary hepatocytes), for example, on a silica/HEMA hybrid, is greater than attachment on HEMA alone. Cell proliferation on these substrates is low compared to cells cultured on TCT (see FIG. 9), with the cells taking on a more 3-D morphology rather than flat and spreading on the substrate. The dry coatings were not subjected to UV-ozone treatment here since they were substantially or completely water insoluble.

Example 7

Post Treatment Overcoat Procedure TMOS (1 mL) was added to deionized water (49 mL) and mixed until the solution was homogeneous (typically about 5 to 10 minutes). The solution was pipetted onto previously prepared hydrogel surface coatings such as described above and allowed to stand for 2 hours under ambient conditions. The residual TMOS pour-over solutions were then removed and the resulting coatings were washed with deionized water and heated in a 60° C. oven until dry.

Example 8

Copoly(HEMA-HEMA Phosphate) An acrylate copolymer, copoly(HEMA-HEMA phosphate) having from about 90 or 95 mol % HEMA and from about 10 or 5 mol % of HEMA-phosphate monomers, was prepared by combining HEMA and HEMA-phosphate monomers in a mole ratio of, for example, 9 to 1 or 9.5 to 0.5 in a 500 mL two-necked round bottomed flask with 125 mL ethanol. The flask was purged with nitrogen, then 130 mg azobisisobutyronitrile (AIBN) free radical source was added to the monomer mixture with magnetic stirring. The solution was heated to 60° C. and allowed to stir 16 hours under nitrogen. The product was precipitated by the dropwise addition into 2 L of vigorously stirred hexane. The resulting suspension was filtered, the solid air dried, and further dried 16 hours at 60° C. to remove residual solvent.

Copoly(HEMA-HEMA phosphate) and Silica sol-gel Coating Copoly(HEMA-HEMA phosphate) containing 5 wt % HEMA-phosphate monomer, and copoly(HEMA-HEMA phosphate) containing 10 wt % HEMA-phosphate monomer as a 1:1 mixture were dissolved in ethanol (1 wt %) by stirring 16 hrs at room temperature. Into two separate 50 g portions of the copoly(HEMA-HEMA phosphate) solution, TMOS was added with stirring in amounts of 0.05 mL (5:1, w:v) and 0.25 mL (1:1, w:v), respectively. After approximately 10 minutes, the combined copoly(HEMA-HEMA phosphate) and silica solutions were added to wells of various well plate formats as mentioned above. The covered (lid on) solution was allowed to evaporate 16 hrs at room temperature, followed by 60° C. for 8 hours, until dry. The plates were sterilized by UV irradiation (1 hr @ 366 nm) prior to packaging, just prior to use, or both. The dry coatings were not subjected to UV-ozone treatment since they were substantially or completely water insoluble.

FIG. 9 show 24 hr cell attachment results of primary hepatocyctes as measured by LDH assay: 905 is 5P/TMOS-5:1 (w:v); 906 is 5P/10P/TMOS-5:5:2 (w:w:v); 907 is 10P/TMOS-5:1 (w:v); 908 is 5P/TMOS-1:1 (w:v); 909 is 5P/10P/TMOS-1:1:2 (w:w:v); 910 is 10P/TMOS-1:1 (w:v); and 911 is HEMA/TMOS-1:1 (w:v).

Example 9

Copoly(HEMA-HEMA phosphate) Only Coating Example 8 was repeated with the exception that no silica was combined with the phosphate copolymer with the result that the 24 hr cell attachment results were considerably lower compared to the coating having the combined phosphate copolymer and silica. In FIG. 9: 901 is a collagen type-I control; 902 is 5P; 903 is 5P/10P-1:1 (w:w); and 904 is 10P.

Example 10

Dextran-based substrate coating Dextran was selected as the polymer and separately processed according to Examples 5 and 6 with the result that a suitable substrate coating was obtained that was suitable for cell culture.

Example 11 (prophetic)

3D porous material A 3D porous scaffold can be obtained with crosslinked HMHEC. This scaffold can be made using a variety of different methods including freeze thawing and freeze drying, which are typical methods to obtain porous material for polysaccharides such as alginates. Alternatively, a solution containing HMHEC can be electrospun to create a web-like scaffold.

Example 12 (prophetic)

Functionalization using maleimide chemistry, esterification, functionalization of biological macromolecules, or increase of specific interchain interactions This example demonstrates the feasibility of appending biologically relevant molecules, such as peptides, growth factors (such as HGF), antioxidants, glycans, or like molecules, to a cellulose polymer to modify cellular attachment, function, proliferation, or combinations thereof. The polysaccharide polymer can be modified using known carbohydrate and polymer functionalization techniques to allow for the attachment of one or more of a variety of macromolecules. For example, one can directly incorporate a maleimide functional group using a Mitsunobu reaction ($PPh_3$, diethyl azodicarboxylate as catalyst) so that one can easily and selectively attach a thiol-containing molecule (e.g., a cysteine modified polypeptide) to the polymer. Alternatively, one can use any thiol containing compound to add another functional group of interest if a spacer is necessary for proper ligand display. Surface properties can be adjusted by different methods of modification/functionalization through either the organic (polymer) portion or inorganic (silica) portion of the hybrid material.

An abundance of hydroxy groups allows for polymer modification using ester formation using coupling reagent combinations, such as EDC/NHS (N-(3-Dimethylaminopropyl)-N'-ethylcarbodiimide and N-Hydroxysulfosuccinimide) or like other carbodiimide coupling reagents. A preactived carboxylic acid such as a succinimide ester or p-nitrophenol ester can also be used in the absence of the coupling reagents.

Any of the aforementioned chemistries or other chemistries (see Zhang, L.-M. Carbohydr. Polym., 2001, 45, 1-10) can also be used to further modify the polymer with hydrophobic groups. This hydrophobic modification can increase the hydrophobic interactions between neighboring polysaccharide chains and allow for control of cell culture time and cell release on these substrates. Other self-associating groups such as perfluoroalkyl or silicones can be incorporated to provide cohesion, but not cell adhesion, particularly if the interest is in probing specific ligand-receptor interactions.

The disclosure has been described with reference to various specific embodiments and techniques. However, it should be understood that many variations and modifications are possible while remaining within the scope of the disclosure.

What is claimed is:

1. A cell culture surface coating comprising:
   an hydrogel comprised of a water insoluble polymer comprised of a hydrophobe modified carbohydrate, an hydroxylated acrylate, or a combination thereof; and
   an over-coat layer comprised of a silica source component.

2. The coating of claim 1, wherein the water insoluble polymer comprises a UV-ozone treated water soluble polymer comprised of the hydrophobe modified carbohydrate.

3. The coating of claim 1, further comprising a silica source.

4. The coating of claim 3, wherein the water insoluble polymer comprises a UV-ozone treated water soluble polymer comprised of the hydrophobe modified carbohydrate.

5. The coating of claim 4, wherein the UV-ozone treated product of the combined silica source and water insoluble polymer cell culture surface coating has improved cell attachment and adhesion properties.

6. The coating of claim 3 wherein the silica source comprises a substituted and unsubstituted tetraalkyloxysilane, a substituted and unsubstituted alkyltrialkyloxysilane, or a combination thereof.

7. The coating of claim 1, wherein the water insoluble polymer comprises a hydrophobe modified carbohydrate source selected from an hydroxalkyl cellulose, an hydrophobe modified cellulose, an hydrophobe modified hydroxyalkylcellulose, an hydrophobe modified alkylene oxide modified hydroxyalkylcellulose, or a combination thereof.

8. The coating of claim 1, wherein the hydrophobe modified carbohydrate or the hydroxylated acrylate are substantially free of cross-linking monomers.

9. The coating of claim 8, wherein the hydroxylated acrylate comprises a HEMA polymer, a HEMA copolymer, a HEMA-HEMA phosphate copolymer, or a combination thereof.

10. The coating of claim 1 wherein the water insoluble polymer comprises a UV-ozone-transformed water soluble polymer, a UV-ozone-transformed water swellable polymer, or a combination thereof.

11. The coating of claim 1 further comprising a container.

12. The coating of claim 11, further comprising a three dimensional disposition of the surface coating on a surface of the container.

13. The coating of claim 1, wherein the hydroxylated acrylate polymer comprises an HEMA copolymer comprised of from about 10 to 90 mol % HEMA and from about 1 to about 10 mol % of HEMA-phosphate co-monomer, or a combination thereof.

14. A biosensor coating composition comprising:
an hydrogel comprised of a water insoluble polymer comprised of a hydrophobe modified carbohydrate, an hydroxylated acrylate, or a combination thereof; and an over-coat layer comprised of a silica source component.

15. The biosensor coating composition of claim 14 further comprising a silica source.

* * * * *